United States Patent
Murray et al.

(10) Patent No.: US 10,285,649 B1
(45) Date of Patent: May 14, 2019

(54) WHEELCHAIR MOVEMENT MEASUREMENT AND ANALYSIS

(71) Applicant: Accenture Global Solutions Limited, Dublin (IE)

(72) Inventors: Matt Murray, Austin, TX (US); Eric Bee, Austin, TX (US); Eric Schneider, Austin, TX (US); Marc Boudria, Austin, TX (US); Ben E. Lamm, Austin, TX (US); Tyler Hively, Austin, TX (US)

(73) Assignee: Accenture Global Solutions Limited, Dublin (IE)

( * ) Notice: Subject to any disclaimer, the term of this patent is extended or adjusted under 35 U.S.C. 154(b) by 371 days.

(21) Appl. No.: 15/222,493

(22) Filed: Jul. 28, 2016

Related U.S. Application Data

(60) Provisional application No. 62/197,896, filed on Jul. 28, 2015, provisional application No. 62/339,489, filed on May 20, 2016.

(51) Int. Cl.
*A61B 5/00* (2006.01)
*G01C 9/02* (2006.01)
(Continued)

(52) U.S. Cl.
CPC .......... *A61B 5/6894* (2013.01); *A61B 5/4866* (2013.01); *G01C 9/02* (2013.01);
(Continued)

(58) Field of Classification Search
CPC combination set(s) only.
See application file for complete search history.

(56) References Cited

U.S. PATENT DOCUMENTS

| | | | |
|---|---|---|---|
| 8,996,432 B1 * | 3/2015 | Fu | A61G 5/1056 706/23 |
| 2013/0297220 A1 * | 11/2013 | Yuen | A61B 5/0002 702/19 |

(Continued)

OTHER PUBLICATIONS

Shaffer et al., "SmartHub: A personal fitness tracking device for manual wheelchair users (The Ohio State University)," Jun. 4, 2015. Retrieved from the Internet: URL<http://aac-rerc.psu.edu/wordpressmu/RESNA-SDC/2015/06/04/smarthub-a-personal-fitness-tracking-device-for-manual-wheelchair-users-the-ohio-state-university/>. 7 pages.

(Continued)

*Primary Examiner* — Thomas G Black
*Assistant Examiner* — Ana D Thomas
(74) *Attorney, Agent, or Firm* — Fish & Richardson P.C.

(57) ABSTRACT

Techniques are described for collecting sensor data associated with a wheelchair and, based on the sensor data, determining metric(s) for a user of the wheelchair. Sensor(s) attached to, or in proximity to, the wheelchair may collect sensor data describing the wheelchair and/or its component(s), such as location, velocity, acceleration, direction of movement, orientations (e.g., pitch, yaw, roll), angular velocity of wheels, angular acceleration of wheels, and so forth. The sensor data may be analyzed to determine (e.g., fitness) metrics such as a caloric burn rate, a metabolic burn rate, and/or power expenditure of the user while the user is employing the wheelchair to exercise or otherwise move. The metric(s) and/or sensor data may be presented to the user through a user interface on a smartphone, tablet computer, wearable computer, or other device, to enable the user to monitor fitness metric(s) during use of the wheelchair.

20 Claims, 6 Drawing Sheets

(51) Int. Cl.
*G01P 3/44* (2006.01)
*G01C 19/00* (2013.01)
*G01L 3/24* (2006.01)

(52) U.S. Cl.
CPC .............. *G01C 19/00* (2013.01); *G01L 3/247* (2013.01); *G01P 3/44* (2013.01)

(56) References Cited

U.S. PATENT DOCUMENTS

2015/0351981 A1* 12/2015 Sazonov .............. A61B 5/6894
 297/217.2
2017/0032648 A1* 2/2017 McClain .............. G08B 21/043

OTHER PUBLICATIONS

Gil, "Freewheel is a fitness tracker for wheelchairs," Aug. 17, 2015. Retrieved from the Internet: URL<http://www.wareable.com/saves-the-day/freewheel-is-a-fitness-tracker-for-wheelchairs-1540>. 5 pages.

* cited by examiner

WHEELCHAIR MOVEMENT MEASUREMENT AND ANALYSIS

CROSS-REFERENCE TO RELATED APPLICATION

This application claims priority to U.S. Provisional Patent Application Ser. No. 62/197,896 filed on Jul. 28, 2015, titled "Wheelchair Data Collection Device," and to U.S. Provisional Patent Application Ser. No. 62/339,489 filed on May 20, 2016, titled "Wheelchair Movement Measurement and Analysis," both of which are hereby incorporated by reference in the entirety.

BACKGROUND

Wearable fitness tracking devices have become a popular tool to enable people to track physical activity. Such devices may measure the number of steps or strides taken by an individual, the distance traveled while running or walking, and so forth. Currently available fitness tracking devices are configured to track activity of a person walking or running. Given the different technical challenges inherent in tracking the activity of a person in a wheelchair compared to a person walking or running, the currently available fitness tracking devices are not useable by people who employ a wheelchair to exercise or otherwise move themselves.

SUMMARY

Implementations of the present disclosure are generally directed to measuring and analyzing movement data for a wheelchair or other form of conveyance. More specifically, implementations are directed to collecting sensor data describing the location and/or movement of a wheelchair, or component(s) of the wheelchair, and using the sensor data to determine one or more metrics (e.g., fitness metric(s)) for a user of the wheelchair.

In general, innovative aspects of the subject matter described in this specification can be embodied in methods that include actions of: receiving sensor data determined by sensors in proximity to a wheelchair, the sensor data indicating an inclination of the wheelchair and a rotational frequency of at least one wheel of the wheelchair, the sensors including a gyroscopic orientation sensor to determine the inclination and at least one Hall effect sensor to determine the rotational frequency; determining a force applied to the wheelchair based at least partly on the inclination of the wheelchair; determining at least one metric for a user of the wheelchair based at least partly on the force and the rotational frequency; and presenting the at least one metric through a user interface.

Implementations can optionally include one or more of the following features: determining the at least one metric further includes determining an angular velocity of the at least one wheel, based at least partly on the rotational frequency; determining a power as a product of the force and the angular velocity; and/or determining the at least one metric based on the power; the sensor data further includes location data indicating the location of the wheelchair determined at least partly based on satellite-based navigation signals; the angular velocity is further based at least partly on the location data; the sensor data includes orientation data indicating at least one orientation of the wheelchair other than the inclination, the at least one orientation relative to at least one axis; the orientation data is determined by at least one of the gyroscopic orientation sensor or an accelerometer coupled to the wheelchair; the sensor data includes wheel rotation data indicating the rotational frequency of the at least one wheel of the wheelchair; the wheel rotation data is determined by at least one rotation sensor coupled to the wheelchair in addition to the at least one Hall effect sensor; the at least one metric includes one or more of a caloric burn rate, a metabolic burn rate, or a power expenditure of the user of the wheelchair; the at least one of the sensors is included in a data collection device attached to the wheelchair; and/or the sensor data is received in a communication that is sent over a wireless network from a network interface of the data collection device.

Implementations provide the following advantages. By collecting sensor data describing the movement and/or orientation of a wheelchair during its operation, and by determining metric(s) based on the sensor data, implementations providing information to enable a wheelchair user to monitor their performance during exercise and/or sporting activities. Implementations provide a technical improvement over traditional fitness tracking hardware devices and software, which may not provide useful information to individuals who employ a wheelchair to exercise or play sports, given the particular movements and forms of energy expenditure associated with use of a wheelchair compared to running or walking.

Implementations may be employed to track personal fitness and/or biometric data for athletic training. Implementations may also be employed to train individuals who are new wheelchair users, to help them learn how to use the wheelchair appropriately and efficiently, in a manner that may reduce the risk of stress or injury. The systems and methods described herein may also be used as a (e.g., passive) tool to provide terrain mapping for geographical information systems (GIS) (e.g., Google™ Maps). Implementations can also be used by municipalities and/or other entities to monitor the condition of sidewalks, trails, ramps, handicapped access points, and/or other features of the terrain. Implementations can also be used to assist doctors, nurses, physical therapists, and/or other types of clinicians, such as in a rehabilitation environment in which individuals are recovering from an injury or impairment, and/or learning to use a wheelchair.

Other implementations of any of the above aspects include corresponding systems, apparatus, and computer programs that are configured to perform the actions of the methods, encoded on computer storage devices. The present disclosure also provides a computer-readable storage medium coupled to one or more processors and having instructions stored thereon which, when executed by the one or more processors, cause the one or more processors to perform operations in accordance with implementations of the methods provided herein. The present disclosure further provides a system for implementing the methods provided herein. The system includes one or more processors, and a computer-readable storage medium coupled to the one or more processors having instructions stored thereon which, when executed by the one or more processors, cause the one or more processors to perform operations in accordance with implementations of the methods provided herein.

It is appreciated that aspects and features in accordance with the present disclosure can include any combination of the aspects and features described herein. That is, aspects and features in accordance with the present disclosure are not limited to the combinations of aspects and features specifically described herein, but also include any combination of the aspects and features provided.

The details of one or more implementations of the present disclosure are set forth in the accompanying drawings and the description below. Other features and advantages of the present disclosure will be apparent from the description and drawings, and from the claims.

DESCRIPTION OF DRAWINGS

Like reference symbols in the various drawings indicate like elements.

DETAILED DESCRIPTION

Implementations of the present disclosure include systems, devices, methods, and computer-readable media for collecting sensor data associated with a wheelchair and based on the sensor data determining one or more metrics for a user of the wheelchair. One or more sensors may be attached to, or otherwise in proximity to, a wheelchair. In some implementations, one or more sensors may be included in a data collection device that is permanently or removably attached to the wheelchair. The sensor(s) may collect sensor data describing the movement(s) and/or orientation(s) of the wheelchair and/or component(s) of the wheelchair. In some implementations, the sensor data indicates one or more of the following: a location of the wheelchair (e.g., geographic coordinates); a velocity of the wheelchair; an acceleration of the wheelchair; a direction in which the wheelchair is moving; an orientation of the wheelchair with respect to one or more axes (e.g., pitch, yaw, roll); an angular velocity of one or more wheels of the wheelchair; or an angular acceleration of the wheel(s) of the wheelchair. Sensor data may also describe a user of the wheelchair. For example, biometric sensors worn by or otherwise in proximity to the user may collect information regarding the user's heart rate, blood pressure, perspiration, and/or other biometric data.

The sensor data may be analyzed to determine one or more metrics such as fitness metric(s) for the user. In some implementations, the sensor data is analyzed to determine a caloric burn rate, a metabolic burn rate, and/or power expenditure of the user while the user is employing the wheelchair to exercise or otherwise move. Caloric burn rate represents the energy burned during action by an individual. Metabolic burn rate represents the amount of energy consumed at rest. For example, if an individual has lost a limb or use of a limb the metabolic burn rate can differ by up to 20% compared to the rate when the limb was present or useable. The metric(s) and/or at least a portion of the sensor data may be presented to the user through a user interface (UI) on a smartphone, tablet computer, wearable computer, or any other appropriate computing device. In this way, implementations enable the user of a wheelchair to monitor fitness metric(s) during exercise or sporting activities.

Figure 1:
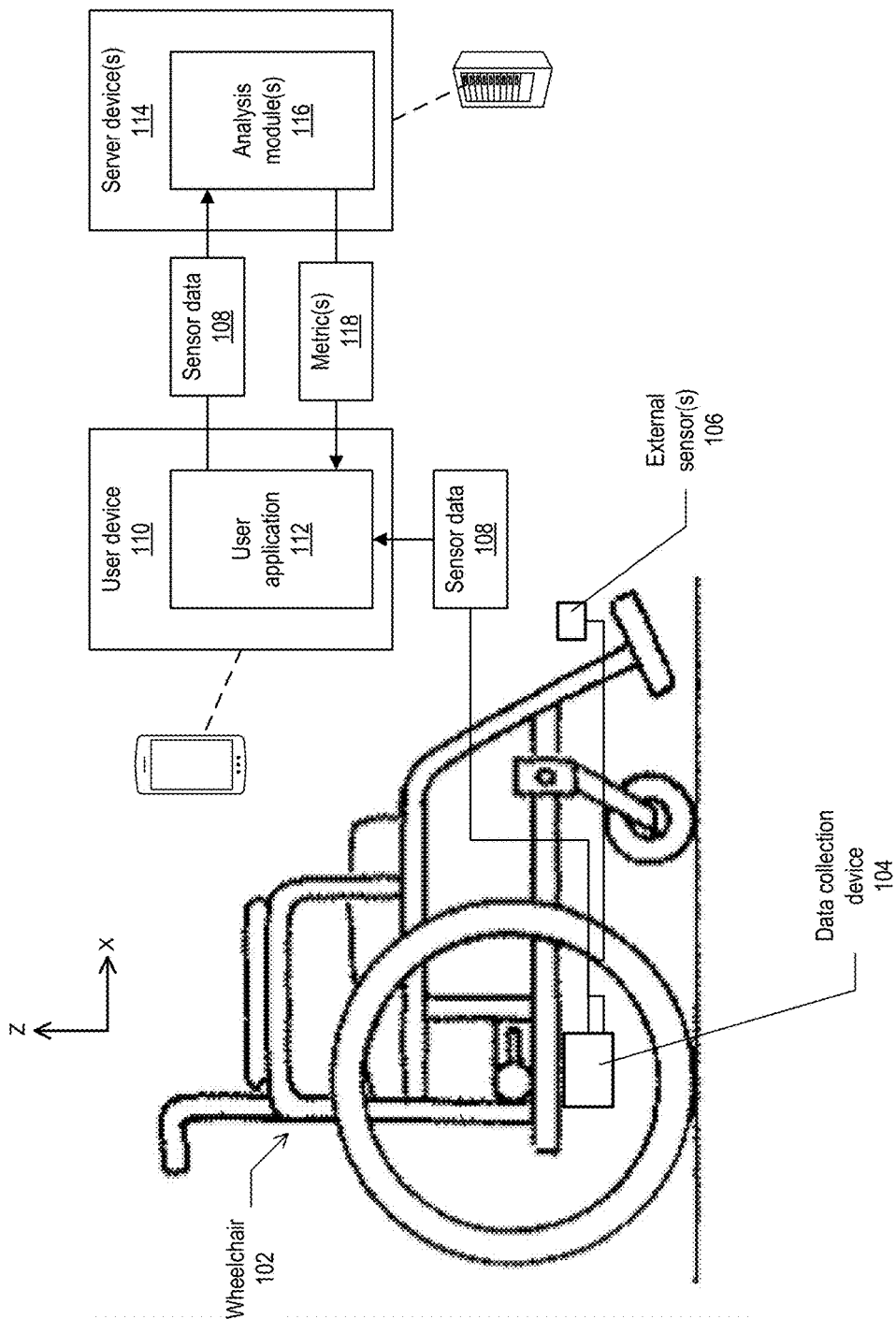
FIG. 1 depicts an example system for collecting and analyzing sensor data associated with a wheelchair to determine one or more metrics, in accordance with implementations of the present disclosure.

FIG. 1 depicts an example system for collecting and analyzing sensor data 108 associated with a wheelchair 102 to determine one or more metrics 118, in accordance with implementations of the present disclosure. In some implementations, a data collection device 104 is attached to the wheelchair 102. The data collection device 104 may include various sensor(s) to collect sensor data 108. In some implementations, the data collection device 104 is permanently attached to the wheelchair 102, e.g., during the manufacture of the wheelchair 102. In some implementations, the data collection device 104 is temporarily attached to the wheelchair 102, such that a user of the wheelchair 102 may remove and reattach the data collection device 104 as desired. The system may also include external sensor(s) 106 that are attached to or otherwise in proximity to the wheelchair 102 and that are external to the data collection device 104. The external sensor(s) 106 may be communicatively coupled with the data collection device 104, over a wired and/or wireless connection, such that the data collection device 104 is able to receive sensor data 108 from the external sensor(s) 106.

The data collection device 104 may receive sensor data 108 from its incorporated sensor(s) and/or the external sensor(s) 106. The data collection device 104 may communicate the sensor data 108 to a user device 110. In some implementations, the data collection device 104 may communicate the sensor data 108 to the user device 110 over one or more wired and/or wireless networks. For example, the data collection device 104 may communicate the sensor data 108 to the user device 110 over a wireless network that supports a version of the Bluetooth™ (BT) and/or Bluetooth Low Energy™ (BTLE) standard. For example, a user may hold or wear the user device 110 while in the wheelchair 102, such that the user device 110 is in proximity (e.g., BT or BTLE signal range) to the data collection device 104. Implementations also support the use of other wireless and/or wired communications standards.

In some implementations, the data collection device 104 is a component that includes sensor(s), processor(s), memory, storage, and/or network interface(s) included in an enclosed package that is easily attached to or removed from a wheelchair 102. In some implementations, the data collection device 104 is attached to the wheelchair 102 such that the presence of the data collection device 104 does not interfere with the normal operations of the wheelchair 102. The data collection device 104 may be attached to allow the wheelchair 102 to be collapsed and/or disassembled, in instances where the wheelchair 102 is designed to be collapsed or at least partly disassembled.

In some implementations, the data collection device 104 may include a power source and/or receive power from an external power supply, to provide power to operate the various components of the data collection device 104. In some instances, the data collection device 104 includes a power source that is a battery. The battery may be rechargeable through an external supply of power and/or through power that is generated through the movement of the wheelchair 102. For example, the rotation of the wheel(s) may cause power generator(s) to generate power to operate the data collection device 104 and/or charge the battery. In some instances, a data collection device 104 may be configured with a form factor (e.g., a modular form factor) designed to attach to a particular model of wheelchair 102 having a particular configuration. The data collection device 104 may be attached, permanently or temporarily, to any appropriate position on the wheelchair 102 that enables the collection of sensor data 108. The data collection device 104 is described further with reference to FIGS. 2A and 2B.

The user device 110 may include any appropriate type of computing device. In some examples, the user device 110 is a mobile and/or portable computing device such as a smartphone, tablet computer, wearable computer, implanted computing device, and so forth. The user device 110 may execute a user application 112. The sensor data 108 may be received through a network interface (e.g., transceiver) of the user device 110 and the sensor data 108 may be accessed by the user application 112. In some implementations, the user application 112 communicates at least a portion of the sensor data 108 to one or more analysis module(s) 116 executing on one or more server devices 114. The server device(s) 114 may include any appropriate type of computing device(s). The analysis module(s) 116 may process the sensor data 108 to determine (e.g., calculate) one or more metric(s) 118 based on the sensor data 108. The metric(s) 118 may be communicated to the user device 110. In some implementations, the metric(s) 118 may be determined, at least in part, by operations performed by the user application 112. The user application 112 may present the metric(s) 118 through a UI such as a graphical user interface (GUI). In some implementations, the UI may also present at least a portion of the sensor data 108. The user application 112 and the UI are described further with reference to FIG. 3.

Figure 2A:
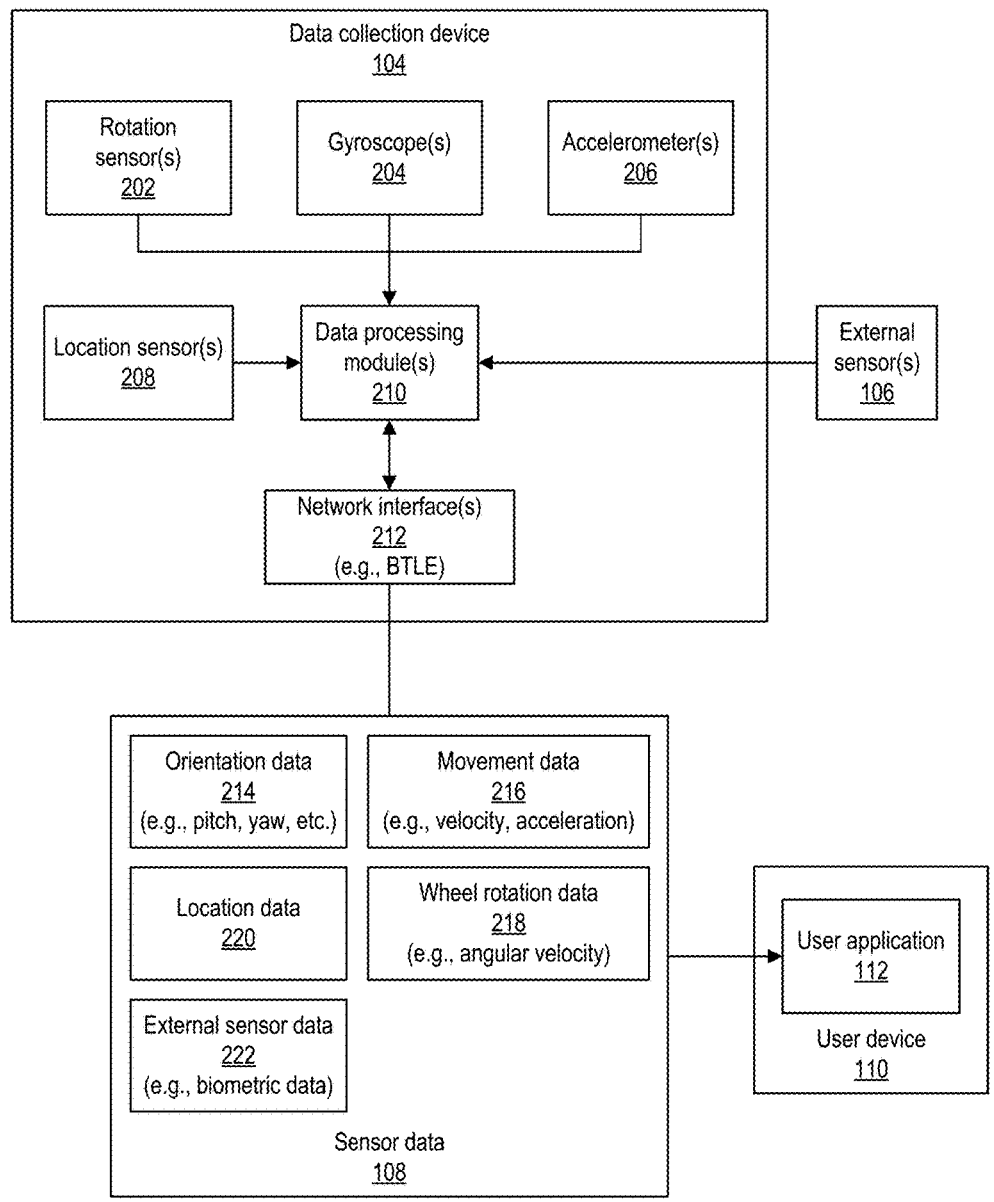
FIG. 2A depicts an example system for collecting and analyzing sensor data associated with a wheelchair, in accordance with implementations of the present disclosure.

FIG. 2A depicts an example system for collecting and analyzing sensor data 108 associated with a wheelchair 102, in accordance with implementations of the present disclosure. As shown in the example of FIG. 2A, the data collection device 104 may include any number of sensors that determine various types of sensor data 108. The sensor data 108 generated by the various sensor(s) may be received by one or more data processing module(s) 210 executed by processor(s) of the data collection device 104. The data processing module(s) 210 may employ network interface(s) 212 of the data collection device 104 to communicate the sensor data 108 to the user application 112 executing on the user device 110. In some implementations, the network interface(s) 212 may employ a BTLE network to communicate the sensor data 108. In some implementations, the data processing module(s) 210 may also perform various operation(s) to process the sensor data 108 to determine metric(s) 118, and/or perform at least some of the operation(s) described below for calculating the metric(s) 118.

In some implementations, the data collection device 104 includes one or more rotation sensor(s) 202 that generate wheel rotation data 218 describing the rotation of one or more wheels of the wheelchair 102. In some implementations, the wheel rotation data 218 may indicate a rotational frequency for each wheel as a number of rotations of the wheel in a particular time period. The wheel rotation data 218 may include an angular velocity of each wheel and/or an angular acceleration of each wheel. The rotation sensor(s) 202 may include a sensor for each wheel of the wheelchair 102.

In some implementations, the rotation sensor(s) 202 include Hall effect sensor(s) that determine the wheel rotation data 218 by measuring a Hall effect. A Hall effect is the generation of a voltage difference in an electrical conductor, the voltage difference being transverse to an electric current in the conductor and also transverse to a magnetic field in proximity to the conductor. In some implementations, a magnet may be attached to each of one or more wheels (e.g., to a spoke of the wheel) such that the magnet revolves around the axis of the wheel as the wheel rotates. A conductor (e.g., a wire) may be arranged such that the magnet passes by the conductor as the wheel rotates. A voltage difference may be generated in the conductor by the Hall effect as the magnet passes, and the voltage difference may be detected by the rotation sensor 202. Based on the periodic detection of the voltage difference, a rotational frequency such as rotations per minute (RPM) of the wheel may be determined. A rotational velocity and/or rotational acceleration of the wheel may also be determined based on the periodic detection of the voltage difference. The voltage difference generated by the Hall effect may exhibit a time variation that is a step pattern such that the voltage is one value when the conductor is in proximity to the magnet and the voltage is a different (e.g., lower) value when the conductor is not in proximity the magnet. In some implementations, this voltage data may be programmatically altered by the rotation sensor(s) 202 or by the data processing module(s) 210 to generate a pulse at a time corresponding to the leading (or falling) edge of the step pattern. This alteration (e.g., a derivative) may facilitate the timing measurement to determine the rotational frequency, angular velocity, and/or angular acceleration of the wheel(s). For example, a rotational frequency of the wheel may be determined based on the period separating the pulses.

Implementations also support the use of other types of sensor(s) for the rotation sensor(s) 202. For example, the rotation sensor(s) 202 may include light sensor(s) that detect periodic change in received light caused by the rotation of the wheel, such as light periodically passing through gaps between spokes in a wheel. As another example, the rotation sensor(s) may include sound detectors that determine the wheel rotation data 218 based on detected patterns in the sound generated by the rotating wheel. In some implementations, the rotation sensor(s) 202 may be incorporated into the wheelchair 102, e.g., as external sensor(s) 106, and configured to employ a capacitance measurement to detect the rotation of the wheel(s).

The sensor(s) may also include one or more accelerometers 206 that determine movement data 216 indicating the speed and/or acceleration of the wheelchair 102. One or more gyroscopes 204 may determine orientation data 214 that indicates the orientation of the wheelchair 102 relative to one or more axes. The gyroscope(s) 204 may also be described as gyroscopic orientation sensor(s). Orientation data 214 may indicate the angle of orientation (e.g., roll) of the wheelchair 102 relative to an axis that runs from the front to the back of the wheelchair 102. This axis is shown as the X axis in FIG. 1. Such data may indicate whether the wheelchair 102 is tilted to one side or the other. Orientation data 214 may indicate the angle of orientation (e.g., pitch) of the wheelchair 102 relative to an axis that runs from the left side to the right side of the wheelchair 102. This Y axis is perpendicular to the X and Z axes shown in FIG. 1. Such data may indicate whether the wheelchair 102 is inclined forward or backward, e.g., whether the wheelchair 102 is on a downward or upward slope. Orientation data 214 may indicate the angle of orientation (e.g., yaw) of the wheelchair 102 relative to an axis that runs vertically through the wheelchair 102. This axis is shown as the Z axis in FIG. 1. Such data may indicate a direction in which the wheelchair 102 is facing. In some examples, the direction in which the wheelchair 102 is facing may be determined at least in part by a compass or other type of sensor that determines the direction relative to the geomagnetic field.

In some implementations, the sensor(s) include location sensor(s) 208 that determine location data 220 describing a location of the wheelchair 102. The location sensor(s) 208 may include a transceiver arranged to receive and process signals from a satellite-based navigation system such as the Global Positioning System (GPS). The location sensor(s) 208 may determine the location of the wheelchair 102 as a set of geographic coordinates, such as latitude and longitude. Implementations also support the use of other techniques for determining the location of the wheelchair 102, such as inertial navigation systems, determining location based on detected wireless network(s), and so forth.

In some implementations, the location data 220 includes altitude information describing an altitude (e.g., elevation) of the wheelchair 102 with respect to a reference altitude. For example, the location sensor(s) 208 may include a barometer or other type of sensor that measures the air pressure in the vicinity of the wheelchair 102, and the air pressure may be employed to determine the altitude of the wheelchair 102 (e.g., relative to sea level).

In some implementations, the sensor data 108 may be sent to the user device 110, and the user application 112 may access additional sensor data 108 that is collected by sensor(s) that are incorporated into the user device 110 and/or external to the user device 110. For example, location data 220 may be determined at the user device 110 by location sensor(s) 208 incorporated into the user device 110, such as a GPS transceiver, a barometer, and/or other sensor(s), instead of or in addition to the location data 220 determined by location sensor(s) 208 of the data collection device 104.

In some implementations, the sensor data 108 may include external sensor data 222 determined by external sensor(s) 106. The external sensor(s) 106 may be external to the data collection device 104 and communicatively coupled to the data collection device 104 through wired and/or wireless network(s). For example, the external sensor(s) 106 may employ a BLTE connection to communicate the external sensor data 222 to the data collection device 104 and the data processing module(s) 210. As another example, a serial cable or other wired connection may be used to send the external sensor data 222 to the data collection device 104 and the data processing module(s) 210. External sensor data 222 may include biometric data determined by monitoring physiological characteristic(s) of the user of the wheelchair 102. In some implementations, the external sensor data 222 includes heart rate data that indicates a heart rate (e.g., pulse) of the user. The heart rate data may be collected by a heart rate monitor worn by the user, on the user's ankle or other body part. External sensor data 222 may also include other types of biometric data, such as perspiration measurements, blood pressure, brain wave activity, blood sugar level, and so forth. In some implementations, the external sensor(s) 106 may be included in a wearable device (e.g., a wearable fitness tracker) that collects and communicates the external sensor data 222 to the data collection device 104. The sensor data 108 may also include other types of data.

Figure 2B:
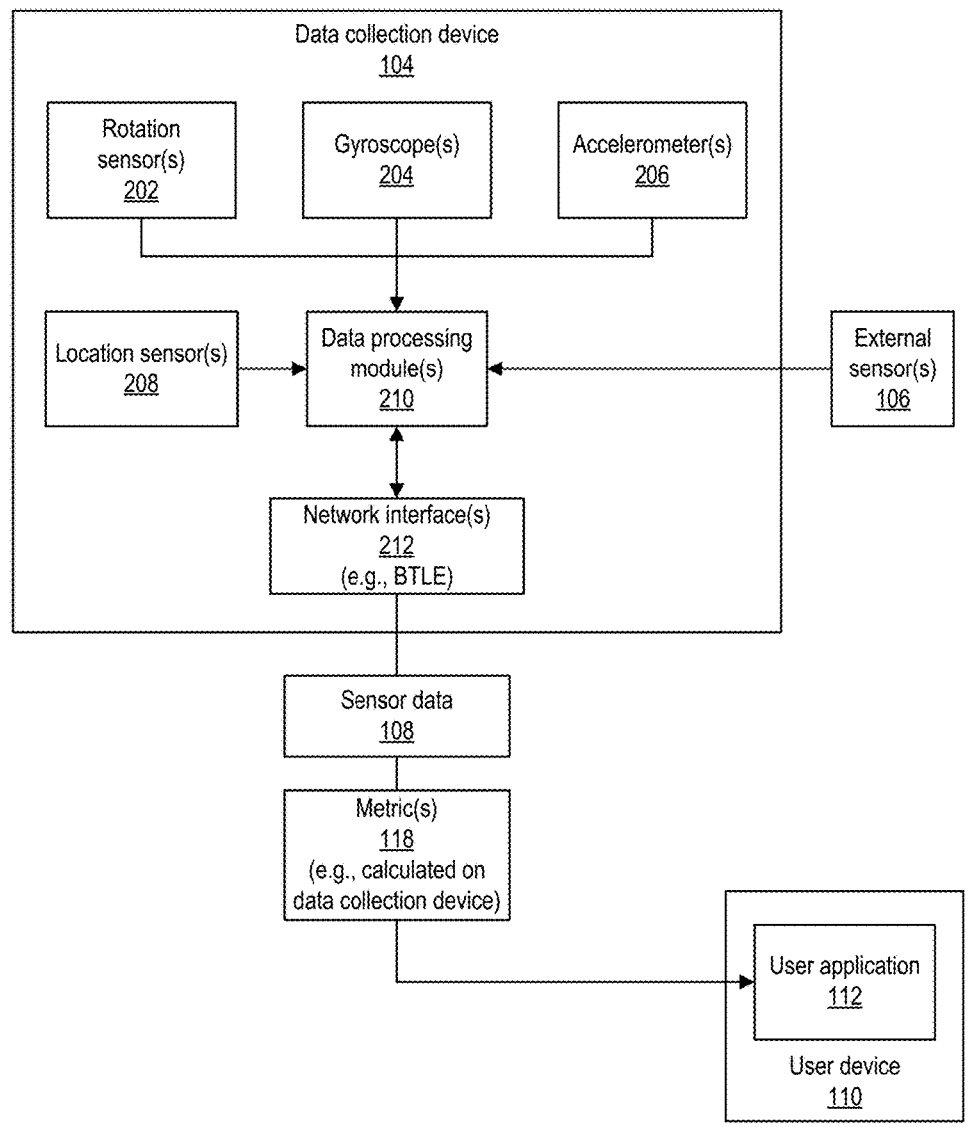
FIG. 2B depicts an example system for collecting and analyzing sensor data associated with a wheelchair, in accordance with implementations of the present disclosure.

FIG. 2B depicts an example system for collecting and analyzing sensor data associated with a wheelchair, in accordance with implementations of the present disclosure. As shown in FIG. 2B, in some implementations at least a portion of the sensor data 108 may be processed (e.g., locally) by the data processing module(s) 210 on the data collection device 104. For example, the data processing module(s) 210 may calculate metric(s) 118 such as caloric burn, energy or power expenditure, and/or metabolic burn, based on at least a portion of the sensor data 108. The determined metric(s) 118 and/or the sensor data 108 may be communicated to the user device 110 for presentation in the UI of the user application 112.

Implementations support the use of various techniques for determining the metric(s) 118 based on the sensor data 108. Operations for determining the metric(s) 118 may be performed by the data processing module(s) 210 executing on the data collection device 104, the user application 112 executing on the user device 110, and/or the analysis module(s) 116 executing on the server device(s) 114.

To calculate the energy expended in moving a wheelchair 102 with a user in it, implementations may determine a total mass that is the sum of the mass of the wheelchair 102 and the mass of the user. In some implementations, a user may enter their mass and/or the mass of the wheelchair 102 through the UI of the user application 112. In some implementations, a user may specify the model, brand, and/or other identification of the wheelchair 102, and original equipment manufacturer (OEM) data may be accessed that indicates the mass of the particular wheelchair 102 being used. Implementations may calculate the force needed to move the total mass of the user and wheelchair 102. Such calculations may take into account the slope or include of the wheelchair 102, as described by the orientation data 214. The calculations may employ a rolling friction coefficient (e.g., 1.005 Newtons) in calculating the force, to account for the friction between the wheelchair 102 and the surface it is on. Given the force, implementations may calculate what torque the user applies to the edge of the wheel(s) to achieve that force. Power (e.g., work over time) may be calculated based on the applied torque over time, the velocity, and the wheel radius. The calculated power expenditure (e.g., in Joules) may be converted into a food caloric burn metric.

In some implementations, velocity may be described in meters per second (m/s), wheel diameter may be described in meters (m), time may be described in seconds (s), mass may be described in kilograms (kg), slope may be described in radians of angle, and acceleration may be described in meters per seconds squared (m/s$^2$). Implementations also support the use of any other appropriate units of measurement. The force (in Newtons) may be calculated according to Example Formula 1.

$$N=\text{abs}(m*\sin\theta)+\text{abs}(1.005*\cos\theta*g*m) \quad \text{Example Formula 1}$$

In Example Formula 1, N is the calculated force, m is a total mass of the user and wheelchair 102, 1.005 is the rolling friction coefficient, g is the acceleration of gravity (e.g., 9.8 m/s$^2$), and θ is the angle of inclination (e.g., slope) in radians. Absolute value is abbreviated to abs and cosine is abbreviated to cos.

Implementations may determine the distance traveled by the wheelchair 102 in a period of time as a product of the velocity (e.g., as indicated by the movement data 216) and the amount of time. The distance traveled may also be determined based on the changing location data 220 over time. The circumference of a wheel may be calculated as the product of the wheel diameter and π. The wheel diameter may be retrieved from OEM data for the wheelchair 102 and/or input by the user through the UI of the user application 112. The number of rotations of the wheel(s) during a period of time may be calculated as the distance traveled by the wheelchair 102 divided by the circumference of the wheel(s). The number of rotations may also be determined based on the wheel rotation data 218.

In some implementations, the number of rotations may be used to determine force and/or angular velocity during a turning of the wheelchair 102. When the wheelchair turns the wheels partially rotate. Using the angular velocity that is determined based on distance traveled, instead of or in addition to angular velocity determined based on a rotary encoder (e.g., Hall effect sensors), may provide better fidelity in the calculations in instances where the wheelchair 102 is turning.

The angular velocity of the wheel(s) of the wheelchair 102 may be calculated based on the number of rotations, according to Example Formula 2.

$$\text{angular velocity} = \frac{(\text{rotations} * 2 * \pi)}{\text{time}} \qquad \text{Example Formula 2}$$

Power may be calculated as a product of the force and the angular velocity. The caloric burn rate (e.g., in calories per second) may be calculated as the power divided by the number of Joules per food calorie (e.g., 4184). The power and/or caloric burn rate may be included in the metric(s) 118. The metric(s) 118 may also include other value(s) that quantify characteristic(s) of the user while using the wheelchair 102, such as a metabolic burn rate.

In some implementations, the determination of metric(s) 118 may be further based on other information regarding the user, such as the user's age, gender, weight, height, biometric data, and so forth. Biometric information (e.g., heart rate) in the sensor data 108 may be employed to gauge the user's activity level. In some implementations, information regarding the terrain may be employed in determining the metric(s) 118. For example, more exertion may be needed to move the wheelchair 102 over gravel or grass compared to pavement, and implementations may take the added difficulty into account when calculating metric(s) 118. Terrain information may be retrieved from a datastore, based on the location of the wheelchair 102. In some implementations, data from the accelerometer(s) 206 may be employed to determine the terrain, or at least a roughness or smoothness of the terrain, based on the acceleration(s) of the wheelchair 102 caused by bumps, vibrations, vertical displacements, irregular surfaces, and so forth.

Figure 3:
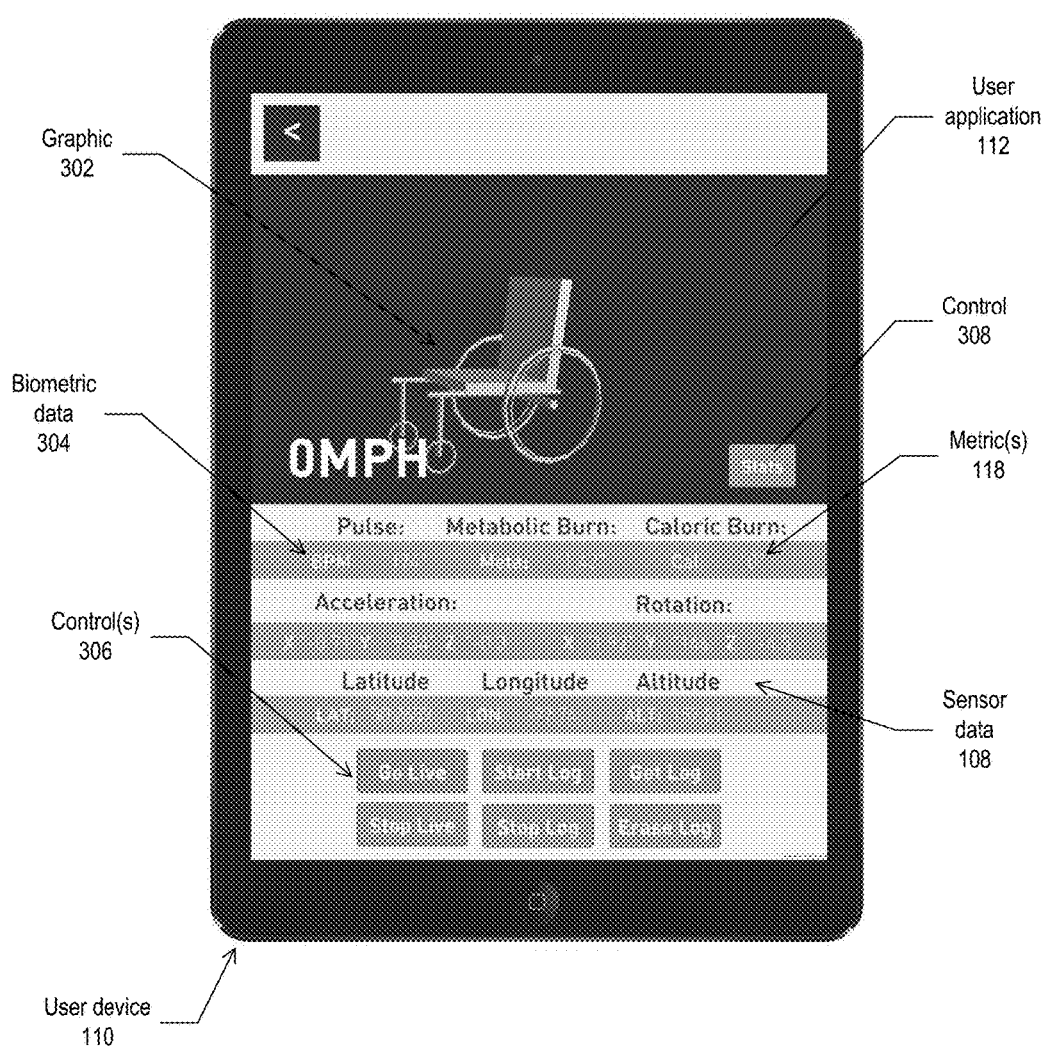
FIG. 3 depicts an example user interface that presents metric(s) and/or sensor data, in accordance with implementations of the present disclosure.

FIG. 3 depicts an example UI that presents metric(s) 118 and/or sensor data 108, in accordance with implementations of the present disclosure. The example UI may be presented by the user application 112 executing on the user device 110. In some implementations, as shown in FIG. 3, the UI may present a graphic 302 of the wheelchair 102. The graphic 302 may indicate the orientation of the wheelchair 102 according to current, or recently collected, orientation data 214. For example, the graphic 302 may depict the wheelchair 102 with a pitch, yaw, and/or roll indicated by the orientation data 214.

The UI may present biometric data 304, such as the heart rate (e.g., pulse) of the user as indicated by current, or recently collected, external sensor data 222. The UI may also present one or more calculated metrics 118 such as the power expenditure, caloric burn rate, and/or metabolic burn rate determined based on the sensor data 108. In some implementations, the UI may present at least a portion of the sensor data 108. For example, as shown in FIG. 3 the UI may present numeric value(s) for the acceleration of the wheelchair 102 with respect to one or more (e.g., three) reference axes. The UI may present numeric value(s) for the orientation of the wheelchair 102 (shown as "Rotation" in FIG. 3). The UI may also present location information, such as the latitude, longitude, and/or altitude of the wheelchair 102 according to current, or recently collected, location data 220.

In some implementations, the UI may include one or more controls 306. The control(s) 306 may include buttons or other UI elements that enable a user to send commands to the UI. For example, the user may employ the control(s) 306 to go live or stop live, e.g., begin or end the presentation of current, or most recently available, sensor data 108 and/or metric(s) 118. The user may employ the control(s) 306 to start log or stop log, e.g., begin or end the storage of sensor data 108 and/or metric(s) 118 in a log file. The user may also employ the control(s) 306 to get log or erase log, e.g., to retrieve and present previously logged data in the UI, or delete a log from storage.

In some implementations, the UI may include a control 308 that causes the UI to present statistics regarding the user and/or wheelchair 102. Such statistics may include the user's age, gender, height, weight, or other information. The statistics may also include the brand and/or model of the wheelchair 102, as well as the mass, wheel diameter, or other characteristics of the wheelchair 102.

The FIG. 3 depicts the UI of the user application 112 as including a particular set of UI elements, such as text, control(s), graphic(s), and so forth, in a particular arrangement, implementations are not limited to the depicted example. The UI may include any appropriate number and any appropriate type of UI elements, in any appropriate arrangement.

Figure 4:
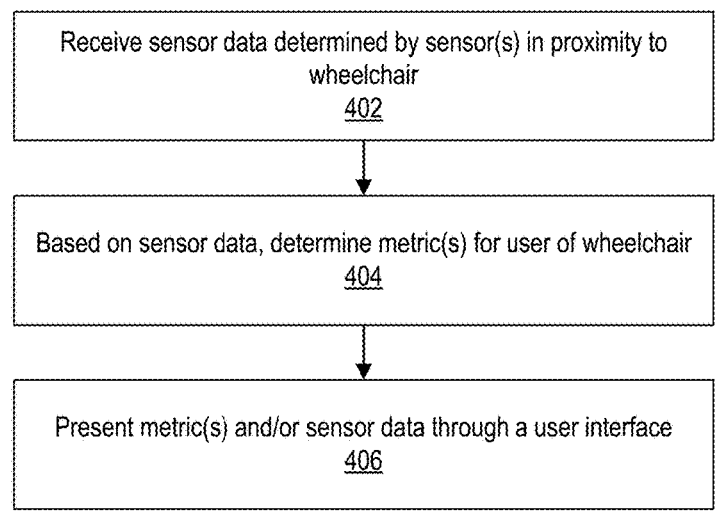
FIG. 4 depicts a flow diagram for an example process for collecting and analyzing sensor data associated with a wheelchair to determine one or more metrics, in accordance with implementations of the present disclosure.

FIG. 4 depicts a flow diagram for an example process for collecting and analyzing sensor data 108 associated with a wheelchair 102 to determine one or more metrics 118, in accordance with implementations of the present disclosure. Operations of the process may be performed by one or more of the data processing module(s) 210, the user application 112, the analysis module(s) 116, or other software module(s) executing on the data collection device 104, the user device 110, the server device(s) 114, or elsewhere.

Sensor data 108 may be received (402). As described above, the sensor data 108 may be determined by one or more sensors in proximity to and/or attached to the wheelchair 102. Based at least partly on the sensor data 108, one or more metrics 118 may be determined (404) for the user. The metric(s) 118 may include fitness and/or exercise metric(s) 118, such as power expenditure, caloric burn rate, metabolic burn rate, and/or others. The metric(s) 118 may be presented (406) through a UI of the user application 112. In some implementations, at least a portion of the sensor data 108 may also be presented as described above.

Implementations may facilitate the training of a user who is inexperienced in using a wheelchair 102, and/or who is inexperienced in using a wheelchair 102 for exercise, sports, or other strenuous activities. The user application 112 may analyze the metric(s) 118 and/or sensor data 108 may make recommendations to the user. For example, the user application 112 may recommend that the user apply torque differently to the wheel(s), perform more or fewer strokes to apply torque, and/or spend more time gliding (e.g., not applying torque). Such recommendation(s) may enable the user to avoid injury, optimize the expenditure of effort, achieve better exercise results, and so forth. Based on the user's statistics, metric(s) 118, and/or sensor data 108, the user application 112 may also make recommendations regarding food and/or water intake, e.g., based on the determined caloric burn rate. The number of strokes in which the user applies torque may be determined based on accelerometer data, e.g., detecting a vibration pattern that characterizes a stroke in which the user applies torque to the wheel(s).

In some implementations, the user application 112, data processing module(s) 210, and/or analysis module(s) 116 may detect conditions when the user may be in peril and/or in need of assistance. For example, based on the orientation data 214 indicating that the wheelchair 102 is on its side, an alert may be sent to a caregiver, emergency service(s), and/or others to aid the user at the current location of the wheelchair 102.

In some implementations, the determination of metric(s) 118 may be further based on information regarding the user's body configuration. For example, the UI of the user application 112 may enable the user to specify that one or more limbs are at least partly atrophied or missing. The calculation of the metabolic burn rate or other metric(s) 118 may take into account the atrophied or missing limb(s). In some implementations, the calculation of the metric(s) 118 may be based on the roll (e.g., the side-to-side incline) of the wheelchair 102 as well as the pitch (e.g., front-to-back incline). In some implementations, the force calculations may be performed independently for each of the wheel(s) of the wheelchair 102.

Although examples herein may describe the wheelchair 102 as having two (e.g., primary) wheel(s), implementations support the use of a wheelchair 102 with any appropriate number of wheels. Implementations may also be employed, with suitable modifications, to collect and analysis movement and/or location data for other types of vehicles, such as bicycles.

In some implementations, sensor data 108 may be collected from one or more wheelchairs 102 as the wheelchair(s) 102 are operated by user(s). The sensor data 108 may be stored, aggregated, analyzed, or otherwise processed to map a region according to its terrain, steepness of incline, altitude, and so forth. For example, sensor data 108 describing location, acceleration, and/or orientation may be analyzed to determine that a particular location (e.g., latitude and longitude) as terrain that is rough (e.g., dirt or gravel trails) or smooth (e.g., pavement). The particular location may also be determined to be steep in inclination (e.g., hilly or mountainous), flat, or any other inclination. Such information regarding local terrain conditions may be aggregated to provide a detailed map of a region that indicates inclination, terrain type, obstacles, and so forth.

The terrain information may be provided to users in wheelchairs, or not in wheelchairs, to facilitate the users' navigation in a region. For example, a biker may want to go on a ride but may also wish to take a route that has particular terrain (e.g., pavement or dirt trails) or inclination (e.g., steep, generally flat, uphill, downhill, etc.). The biker may employ the terrain information to select a route, or an application may recommend a route based on the terrain information. As another example, a wheelchair user may want to reach a public restroom nearby, and may use the terrain information to determine a quickest, most direct route that is not obstructed by stairs or other problematic terrain. The collected terrain data may facilitate the movement of users who have particular constraints and/or criteria regarding how they get around, such as hikers, bikers, skateboarders, the elderly, wheelchair users, and so forth.

In some implementations, the terrain information may be employed by an application (e.g., the user application 112) to provide warnings to users regarding upcoming obstacles, terrain variations, or other features of the terrain. For example, an application may determination that a wheelchair user may encounter impassable stairs, a wall, impassable terrain, or other obstructions if they continue on a current route, and the application may present a warning. The warning may be visual, audio (e.g., a warning sound), and/or haptic (e.g., a vibration of the user device 110).

Figure 5:
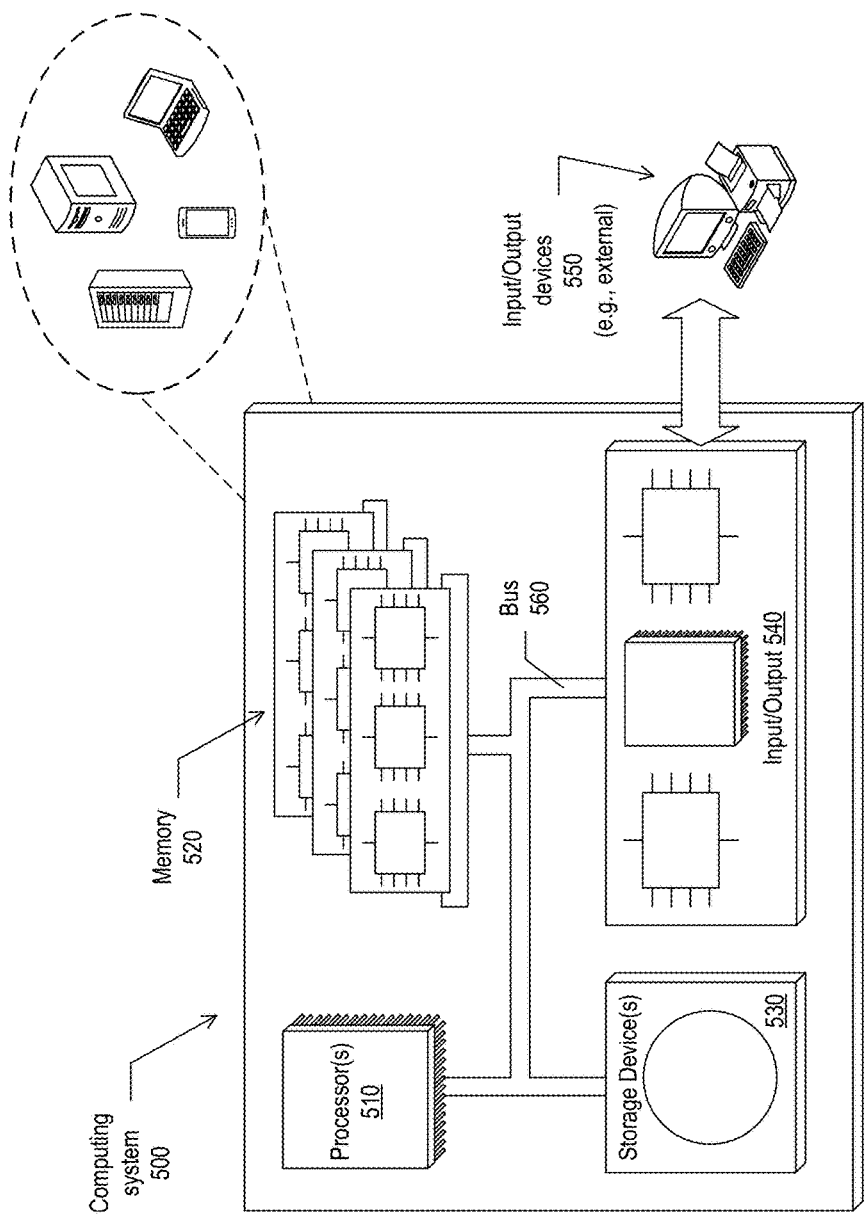
FIG. 5 depicts an example computing system architecture, in accordance with implementations of the present disclosure.

FIG. 5 depicts an example computing system 500 in accordance with implementations of the present disclosure. The system 500 may be used for any of the operations described with respect to the various implementations discussed herein. For example, the system 500 may be included, at least in part, in one or more of the data collection device 104, the user device 110, the server device(s) 114, and/or other device(s) described herein. The system 500 may include one or more processors 510, a memory 520, one or more storage devices 530, and one or more input/output (I/O) devices 550 controllable via one or more I/O interfaces 540. Two or more of the components 510, 520, 530, 540, or 550 may be interconnected via at least one system bus 560, which may enable the transfer of data between the various modules and components of the system 500.

The processor(s) 510 may be configured to process instructions for execution within the system 500. The processor(s) 510 may include single-threaded processor(s), multi-threaded processor(s), or both. The processor(s) 510 may be configured to process instructions stored in the memory 520 or on the storage device(s) 530. The processor(s) 510 may include hardware-based processor(s) each including one or more cores. The processor(s) 510 may include general purpose processor(s), special purpose processor(s), or both.

The memory 520 may store information within the system 500. In some implementations, the memory 520 includes one or more computer-readable media. The memory 520 may include any number of volatile memory units, any number of non-volatile memory units, or both volatile and non-volatile memory units. The memory 520 may include read-only memory, random access memory, or both. In some examples, the memory 520 may be employed as active or physical memory by one or more executing software modules.

The storage device(s) 530 may be configured to provide (e.g., persistent) mass storage for the system 500. In some implementations, the storage device(s) 530 may include one or more computer-readable media. For example, the storage device(s) 530 may include a floppy disk device, a hard disk device, an optical disk device, or a tape device. The storage device(s) 530 may include read-only memory, random access memory, or both. The storage device(s) 530 may include one or more of an internal hard drive, an external hard drive, or a removable drive.

One or both of the memory 520 or the storage device(s) 530 may include one or more computer-readable storage media (CRSM). The CRSM may include one or more of an electronic storage medium, a magnetic storage medium, an optical storage medium, a magneto-optical storage medium, a quantum storage medium, a mechanical computer storage medium, and so forth. The CRSM may provide storage of computer-readable instructions describing data structures, processes, applications, programs, other modules, or other data for the operation of the system 500. In some implementations, the CRSM may include a data store that provides storage of computer-readable instructions or other information in a non-transitory format. The CRSM may be incorporated into the system 500 or may be external with respect to the system 500. The CRSM may include read-only memory, random access memory, or both. One or more CRSM suitable for tangibly embodying computer program instructions and data may include any appropriate type of non-volatile memory, including but not limited to: semiconductor memory devices, such as EPROM, EEPROM, and flash memory devices; magnetic disks such as internal hard disks and removable disks; magneto-optical disks; and CD-ROM and DVD-ROM disks. In some examples, the processor(s) 510 and the memory 520 may be supplemented by, or incorporated into, one or more application-specific integrated circuits (ASICs).

The system 500 may include one or more I/O devices 550. The I/O device(s) 550 may include one or more input devices such as a keyboard, a mouse, a pen, a game controller, a touch input device, an audio input device (e.g., a microphone), a gestural input device, a haptic input device, an image or video capture device (e.g., a camera), or other devices. In some examples, the I/O device(s) 550 may also include one or more output devices such as a display, LED(s), an audio output device (e.g., a speaker), a printer, a haptic output device, and so forth. The I/O device(s) 550 may be physically incorporated in one or more computing devices of the system 500, or may be external with respect to one or more computing devices of the system 500.

The system 500 may include one or more I/O interfaces 540 to enable components or modules of the system 500 to control, interface with, or otherwise communicate with the I/O device(s) 550. The I/O interface(s) 540 may enable information to be transferred in or out of the system 500, or between components of the system 500, through serial communication, parallel communication, or other types of communication. For example, the I/O interface(s) 540 may comply with a version of the RS-232 standard for serial ports, or with a version of the IEEE 1284 standard for parallel ports. As another example, the I/O interface(s) 540 may be configured to provide a connection over Universal Serial Bus (USB) or Ethernet. In some examples, the I/O interface(s) 540 may be configured to provide a serial connection that is compliant with a version of the IEEE 1394 standard.

The I/O interface(s) 540 may also include one or more network interfaces that enable communications between computing devices in the system 500, or between the system 500 and other network-connected computing systems. The network interface(s) may include one or more network interface controllers (NICs) or other types of transceiver devices configured to send and receive communications over one or more networks using any appropriate network protocol.

Computing devices of the system 500 may communicate with one another, or with other computing devices, using one or more networks. Such networks may include public networks such as the internet, private networks such as an institutional or personal intranet, or any combination of private and public networks. The networks may include any appropriate type of wired or wireless network, including but not limited to local area networks (LANs), wide area networks (WANs), wireless WANs (WWANs), wireless LANs (WLANs), mobile communications networks (e.g., 3G, 4G, Edge, etc.), and so forth. In some implementations, the communications between computing devices may be encrypted or otherwise secured. For example, communications may employ one or more public or private cryptographic keys, ciphers, digital certificates, or other credentials supported by a security protocol, such as any version of the Secure Sockets Layer (SSL) or the Transport Layer Security (TLS) protocol.

The system 500 may include any number of computing devices of any appropriate type. The computing device(s) may include, but are not limited to: a personal computer, a smartphone, a tablet computer, a wearable computer, an implanted computer, a mobile gaming device, an electronic book reader, an automotive computer, a desktop computer, a laptop computer, a notebook computer, a game console, a home entertainment device, a network computer, a server computer, a mainframe computer, a distributed computing device (e.g., a cloud computing device), a microcomputer, a system on a chip (SoC), a system in a package (SiP), and so forth. Although examples herein may describe computing device(s) as physical device(s), implementations are not so limited. In some examples, a computing device may include one or more of a virtual computing environment, a hypervisor, an emulation, or a virtual machine executing on one or more physical computing devices. In some examples, two or more computing devices may include a cluster, cloud, farm, or other grouping of multiple devices that coordinate operations to provide load balancing, failover support, parallel processing capabilities, shared storage resources, shared networking capabilities, or other aspects.

The features described may be implemented in digital electronic circuitry or in computer hardware, software, or any combinations of hardware and software. The features may be implemented in at least one computer program product that is tangibly embodied in an information carrier (e.g., a machine-readable storage device) for execution by a programmable processor. The method or process steps may be performed by a programmable processor executing instructions to perform functions of the described implementations by operating on input data and generating output. The described features may be implemented in one or more computer programs that are executable on a programmable system including at least one programmable processor coupled to receive data and instructions from, and to transmit data and instructions to, a data storage system, at least one input device, and at least one output device. A computer program may include a set of instructions that can be used, directly or indirectly, in a computer to perform a certain activity or bring about a certain result. A computer program may be written in any appropriate programming language, including compiled or interpreted languages, and it may be deployed in any appropriate form, including as a stand-alone program or as a module suitable for use in a computing environment.

The logic flows depicted in the figures do not require the particular order shown, or any particular sequential order, to achieve desirable results. In some implementations, other steps may be provided or steps may be eliminated from the described flows. Moreover, the steps may be performed in parallel or serially with respect to other steps. The systems depicted in the figures do not require the particular components, or the particular arrangement of components, shown in the figures. In some implementations, the various systems may include more or fewer components than shown in the figures, and components may be arranged differently to achieve desirable results. Accordingly, implementations other than those explicitly depicted in the figures or described herein are within the scope of the following claims.

A number of implementations of the present disclosure have been described. Nevertheless, it will be understood that various modifications may be made without departing from the spirit and scope of the present disclosure. Accordingly, other implementations are within the scope of the following claims.

What is claimed is:

1. A computer-implemented method performed by at least one processor, the method comprising:
receiving, by the at least one processor, sensor data determined by sensors in proximity to a wheelchair, the sensor data indicating an inclination of the wheelchair and a rotational frequency of at least one wheel of the wheelchair, the sensors including a gyroscopic orientation sensor to determine the inclination and at least one Hall effect sensor to determine the rotational frequency;
determining, by the at least one processor, a force applied to the wheelchair based at least partly on the inclination of the wheelchair;
determining, by the at least one processor, at least one metric for a user of the wheelchair based at least partly on the force and the rotational frequency; and
presenting, by the at least one processor, through a user interface that is executed on a computing device: i) the at least one metric, ii) at least a portion of the sensor data, and iii) a graphic of the wheelchair, the graphic showing the inclination of the wheelchair that is indicated by the sensor data.

2. The method of claim 1, wherein determining the at least one metric further includes:
determining an angular velocity of the at least one wheel, based at least partly on the rotational frequency;
determining a power as a product of the force and the angular velocity; and
determining the at least one metric based on the power.

3. The method of claim 2, wherein:
the sensor data further includes location data indicating the location of the wheelchair determined at least partly based on satellite-based navigation signals; and
the angular velocity is further based at least partly on the location data.

4. The method of claim 1, wherein:
the sensor data includes orientation data indicating at least one orientation of the wheelchair other than the inclination, the at least one orientation relative to at least one axis; and
the orientation data is determined by at least one of the gyroscopic orientation sensor or an accelerometer coupled to the wheelchair.

5. The method of claim 1, wherein:
the sensor data includes wheel rotation data indicating the rotational frequency of the at least one wheel of the wheelchair; and
the wheel rotation data is determined by at least one rotation sensor coupled to the wheelchair in addition to the at least one Hall effect sensor.

6. The method of claim 1, wherein the at least one metric includes one or more of a caloric burn rate, a metabolic burn rate, or a power expenditure of the user of the wheelchair.

7. The method of claim 1, wherein:
the at least one of the sensors is included in a data collection device attached to the wheelchair; and
the sensor data is received in a communication that is sent over a wireless network from a network interface of the data collection device.

8. A system comprising:
at least one processor; and
a memory communicatively coupled to the at least one processor, the memory storing executable instructions which, when executed, cause the at least one processor to perform operations including:
receiving sensor data determined by sensors in proximity to a wheelchair, the sensor data indicating an inclination of the wheelchair and a rotational frequency of at least one wheel of the wheelchair, the sensors including a gyroscopic orientation sensor to determine the inclination and at least one Hall effect sensor to determine the rotational frequency;
determining a force applied to the wheelchair based at least partly on the inclination of the wheelchair;
determining at least one metric for a user of the wheelchair based at least partly on the force and the rotational frequency; and
presenting through a user interface that is executed on a computing device: i) the at least one metric, ii) at least a portion of the sensor data, and iii) a graphic of the wheelchair, the graphic showing the inclination of the wheelchair that is indicated by the sensor data.

9. The system of claim 8, wherein determining the at least one metric further includes:
determining an angular velocity of the at least one wheel, based at least partly on the rotational frequency;
determining a power as a product of the force and the angular velocity; and
determining the at least one metric based on the power.

10. The system of claim 9, wherein:
the sensor data further includes location data indicating the location of the wheelchair determined at least partly based on satellite-based navigation signals; and
the angular velocity is further based at least partly on the location data.

11. The system of claim 8, wherein:
the sensor data includes orientation data indicating at least one orientation of the wheelchair other than the inclination, the at least one orientation relative to at least one axis; and
the orientation data is determined by at least one of the gyroscopic orientation sensor or an accelerometer coupled to the wheelchair.

12. The system of claim 8, wherein:
the sensor data includes wheel rotation data indicating the rotational frequency of the at least one wheel of the wheelchair; and
the wheel rotation data is determined by at least one rotation sensor coupled to the wheelchair in addition to the at least one Hall effect sensor.

13. The system of claim 8, wherein the at least one metric includes one or more of a caloric burn rate, a metabolic burn rate, or a power expenditure of the user of the wheelchair.

14. The system of claim 8, wherein:
the at least one of the sensors is included in a data collection device attached to the wheelchair; and
the sensor data is received in a communication that is sent over a wireless network from a network interface of the data collection device.

15. One or more computer-readable storage media storing instructions which, when executed by at least one processor, cause the at least one processor to perform operations comprising:
receiving sensor data determined by sensors in proximity to a wheelchair, the sensor data indicating an inclination of the wheelchair and a rotational frequency of at least one wheel of the wheelchair, the sensors including a gyroscopic orientation sensor to determine the inclination and at least one Hall effect sensor to determine the rotational frequency;

determining a force applied to the wheelchair based at least partly on the inclination of the wheelchair;

determining at least one metric for a user of the wheelchair based at least partly on the force and the rotational frequency; and presenting through a user interface that is executed on a computing device: i) the at least one metric, ii) at least a portion of the sensor data, and iii) a graphic of the wheelchair, the graphic showing the inclination of the wheelchair that is indicated by the sensor data.

16. The one or more computer-readable storage media of claim 15, wherein determining the at least one metric further includes:

determining an angular velocity of the at least one wheel, based at least partly on the rotational frequency;

determining a power as a product of the force and the angular velocity; and determining the at least one metric based on the power.

17. The one or more computer-readable storage media of claim 16, wherein:

the sensor data further includes location data indicating the location of the wheelchair determined at least partly based on satellite-based navigation signals; and the angular velocity is further based at least partly on the location data.

18. The one or more computer-readable storage media of claim 15, wherein:

the sensor data includes orientation data indicating at least one orientation of the wheelchair other than the inclination, the at least one orientation relative to at least one axis; and the orientation data is determined by at least one of the gyroscopic orientation sensor or an accelerometer coupled to the wheelchair.

19. The one or more computer-readable storage media of claim 15, wherein:

the sensor data includes wheel rotation data indicating the rotational frequency of the at least one wheel of the wheelchair; and the wheel rotation data is determined by at least one rotation sensor coupled to the wheelchair in addition to the at least one Hall effect sensor.

20. The one or more computer-readable storage media of claim 15, wherein the at least one metric includes one or more of a caloric burn rate, a metabolic burn rate, or a power expenditure of the user of the wheelchair.

* * * * *

UNITED STATES PATENT AND TRADEMARK OFFICE
CERTIFICATE OF CORRECTION

PATENT NO. : 10,285,649 B1  
APPLICATION NO. : 15/222493  
DATED : May 14, 2019  
INVENTOR(S) : Matthew Lee Murray et al.

Page 1 of 1

It is certified that error appears in the above-identified patent and that said Letters Patent is hereby corrected as shown below:

On the Title Page

Column 1 (item (72) Inventors), Line 1, delete "Matt Murray" and insert -- Matthew Lee Murray --.

Signed and Sealed this
Nineteenth Day of May, 2020

Andrei Iancu
*Director of the United States Patent and Trademark Office*